United States Patent [19]

Bykadi et al.

[11] Patent Number: 4,927,638
[45] Date of Patent: May 22, 1990

[54] ETOPOSIDE SOLUTIONS

[75] Inventors: Gururaj Bykadi, Phoenix, Ariz.;
Murray A. Kaplan, Syracuse, N.Y.;
Richard G. Corrao, Syracuse, N.Y.;
Edward J. Bara, Syracuse, N.Y.;
Ismat Ullah, Liverpool, N.Y.;
Shreeram N. Agharkar, Fayetteville, N.Y.

[73] Assignee: Bristol-Myers Company, New York, N.Y.

[21] Appl. No.: 243,392

[22] Filed: Sep. 12, 1988

Related U.S. Application Data

[63] Continuation-in-part of Ser. No. 916,599, Oct. 8, 1986, abandoned.

[51] Int. Cl.$^5$ .......................... A61K 9/66; A61K 9/08; C07H 15/20
[52] U.S. Cl. ...................... 424/455; 514/27; 514/35; 514/962; 536/18.1; 424/456
[58] Field of Search .................. 514/27, 35, 962; 424/455, 456; 536/18.1

[56] References Cited

U.S. PATENT DOCUMENTS

| | | | |
|---|---|---|---|
| 3,219,529 | 11/1965 | Nash et al. | 167/65 |
| 3,699,230 | 10/1972 | Beauchamp et al. | 424/272 |
| 4,082,881 | 4/1978 | Chen et al. | 424/241 |
| 4,228,162 | 10/1980 | Luzzi et al. | 424/232 |
| 4,701,327 | 10/1987 | Henmi et al. | 424/455 |
| 4,713,246 | 12/1987 | Begum et al. | 424/455 |
| 4,734,284 | 3/1988 | Terada et al. | 424/455 |

FOREIGN PATENT DOCUMENTS

| | | |
|---|---|---|
| 0161915 | 11/1985 | European Pat. Off. |
| 60-239414 | 11/1985 | Japan . |
| 60-239415 | 11/1985 | Japan . |
| 2155789 | 10/1985 | United Kingdom . |
| 8401506 | 4/1984 | World Int. Prop. O. |

OTHER PUBLICATIONS

M. D'Incalci et al.; Cancer Cemother Pharmacol. 7: 141–145 (1982).
D. J. Stewart et al.; Cancer Treat. Rep. 69:269–273 (1985).

Primary Examiner—Ronald W. Griffin
Assistant Examiner—Nancy S. Carson
Attorney, Agent, or Firm—Mollie M. Yang

[57] ABSTRACT

A solution of etoposide in dimethylisosorbide is disclosed. The solution is useful for filling gelatin capsules and may also be formulated into parenteral dosage forms.

35 Claims, No Drawings

ETOPOSIDE SOLUTIONS

This is a continuation-in-part of U.S. Ser. No. 916,599 filed Oct. 8, 1986, now abandoned, which is hereby incorporated by reference in its entirety.

BACKGROUND OF THE INVENTION

The present invention relates to pharmaceutical compositions. In particular, the invention relates to a solution of etoposide in dimethylisosorbide (DMI).

Etoposide is a semi-synthetic product derived from podophyllotoxin. The material is identified by the chemical name 4'-demethylepipodophyllotoxin-9-(4,6-O(R)-ethylidine-$\beta$-D-glucopyranoside). It is approved by the Federal Food and Drug Administration for use in the treatment of refractory testicular cancer and small cell lung cancer and is currently being marketed under the tradename VePesid ® as an injection solution containing for each ml, 20 mg of etoposide activity (PDR, 42nd Ed., pp. 779–80). The commercial solution is diluted to a manufacturer recommended concentration with an aqueous parenteral vehicle such as 0.9% NaCl, U.S.P. or 5% Dextrose for Injection, U.S.P. before administration by slow intravenous infusion. Etoposide is only sparingly soluble in water, its solubility in water being about 0.1 mg/ml. Thus, in order to prepare a solution of etoposide, an organic solvent or a mixture of organic solvents must be used. The choice of a suitable organic solvent for preparing pharmaceutical dosage forms is further limited to those that have high physiological safety. The marketed etoposide product for parenteral administration is contained in a multi-solvent system.

Etoposide has also been administered to patients via the oral route, either in capsules or as a solution; however, etoposide oral bioavailability is only about 50% of that found after intravenous administration (D'Incalci, M. Cancer Chemother Pharmacol, 7:141–145, 1982; Stewart, D. J. Cancer Treat Rep, 69:269–273, 1985; and Clark, P. I. and Slevin, M. L., Clin. Pharmacokinet, 1987, 12:223–252 at 238–240). Both U.S. Pat. No. 4,713,246 and U.S. Pat. No. 4,734,284 postulate that the low bioavailability of oral etoposide may be attributable to the immediate precipitation of etoposide in aqueous environment, e.g. gastrointestinal fluid; and both references attempt to improve etoposide oral bioavailability by delaying the onset of etoposide precipitation, the former by the addition of taurocholic acid to etoposide solution and the latter by addition of a water-soluble cellulose ether derivative or polyvinylpyrrolidinone.

It has also been suggested that an oral dose twice as high as an IV dose be administered in order to achieve the equivalent blood level (Stewart, D. J., loc. cit.). When high oral does is to be given in capsule dosage form, it is decidedly advantageous to have a concentrated solution of etoposide suitable for encapsulation within a soft or hard gelatin capsule. Such a concentrated solution will enable the preparation of capsules of smaller sizes thereby allowing for easier ingestion; it may also reduce the number of capsules to be swallowed. These factors can become important especially in view of the generally poor physical condition of cancer patients. The currently marketed etoposide solution having 20 mg/ml etoposide activity may be too dilute for the preparation of a convenient capsule dosage form.

Dimethylisosorbide (DMI) has been used as solvent for tetracyclines (U.S. Pat. No. 3,219,529), muscle relaxants (U.S. Pat. No. 3,699,230), steroids (U.S. Pat. No. 4,082,881), and aspirin (U.S. Pat. No. 4,228,162). DMI is miscible with water, ethanol, propylene glycol, isopropyl myristate, diethyl ether, acetone, corn oil, cottonseed oil, etc., and has a very good toxicity profile.

An object of the present invention is to provide a solution of etoposide in DMI. A concentrated solution is particularly suited as filling solution for gelatin capsules. The solution may also be formulated for parenteral use providing an elegant alternative to the complex multicomponent product currently being marketed.

SUMMARY OF THE INVENTION

The present invention is concerned with an etoposide solution which comprises etoposide in dimethylisosorbide. The solution may be formulated into dosage forms for parenteral use; it may also be encapsulated within a soft or hard gelatin capsule, or formulated into other oral dosage forms.

A further aspect of the present invention provides a preferred solution for encapsulation which contains in addition taurocholic acid or a pharmaceutically acceptable salt thereof.

DETAILED DESCRIPTION OF THE INVENTION

Etoposide exhibits an unexpectedly high solubility in DMI. Table I compares the solubility of etoposide in various solvents:

TABLE I

| Solvent | Etoposide Solubility mg/ml |
|---|---|
| Ethanol | <1.0 |
| Benzyl Alcohol | 104 |
| Propylene Glycol | 11 |
| Water | 0.1 |
| Dimethylisosorbide | 320 |

The composition of the present invention is prepared by dissolving the desired components in dimethylisosorbide. The resulting solution is then filtered and the filtrate collected.

The amount of etoposide contained in the solution of this invention is not specifically restricted but may be any amount convenient for pharmaceutical purposes, and may be selected according to the dosage form to be prepared. A preferred capsule filling solution contains from about 50 mg to about 320 mg of etoposide activity per ml of solution. Another preferred solution contains from about 10 mg to about 50 mg of etoposide activity per ml, and may be used to formulate parenteral dosage forms.

A pharmaceutically acceptable acid is preferably included in the solution of the present invention. Any pharmaceutically acceptable acid may be used; for example mineral acids such as hydrochloric acid; and organic carboxylic acids, such as tartaric, citric, succinic, fumaric, or maleic acids. An organic caboxylic acid is preferred, and citric acid is most preferred. The amount used may be from about 0.005 to about 0.5 parts by weight of acid per part by weight of etoposide and preferably from about 0.01 to about 0.02 part by weight of acid per part by weight of etoposide. Citric acid is preferably used in a proportion of from about 0.05 to about 0.1, most preferably about 0.08 part by weight per part by weight of etoposide, and about 0.1 part by weight in the presence of taurocholic acid or a pharmaceutically acceptable salt thereof.

Another aspect of the invention provides a preferred etoposide solution for oral administration comprising etoposide, taurocholic acid, or a pharmaceutically acceptable salt thereof, polyethylene glycol, water, and dimethylisosorbide. The solution preferably contains a second acid and optically a buffer to maintain the acidity of the solution; example of a suitable combination is citric acid and sodium acetate. The solution may be suitably used as fill for capsules, including hard gelatin capsules and soft gelatin capsules.

Taurocholic acid or a pharmaceutically acceptable salt such as sodium taurocholate is included in an amount of from 1 to 10 parts by weight per part by weight of etoposide. Polyethylene glycol having a molecular weight of about 200 to about 600 may be used in the composition. Polyethylene glycol having a molecular weight of about 200–300 is preferred because of its lower viscosity and ease in handling during pharmaceutical manufacturing. The amount of polyethylene glycol may be from 1 to 10 parts by weight relative to etoposide. Water is included in an amount sufficient to solubilize taurocholic acid or its salt and is generally in an amount of 0.1 2 parts by weight per part by weight of etoposide. Dimethylisosorbide may be used in an amount of 1 to 10 parts by weight per part by weight of etoposide.

The composition may optionally contain additional agents that may aid in solubilizing etoposide. Such a cosolvent may be a lower alkanol such as ethanol or glycerol; or glycol such as propylene glycol. When the taurocholic acid containing solution is intended for filling soft gelatin capsules, it is advantageous to include a gelatin plasticizer such as glycerol or propylene glycol in order to prevent hardening of the capsule shell.

The composition may optionally contain other ingredients that may further delay the precipitation of etoposide, for example surfactants. Surfactants generally known as poloxamers may be mentioned as useful for this purpose; a suitable poloxamer is for example poloxamer 407 (supplied by BASF Wyandotte as Pluronic F-127®).

It will be appreciated that a solution of the present invention may contain additional substances so as to confer some particularly desirable pharmaceutical or pharmacological properties to the dosage forms prepared. Examples of additives are antibacterial agents, stabilizers, buffers, and the like.

A preferred embodiment of an etoposide solution in dimethylisosorbide containing taurocholic acid or a pharmaceutically acceptable salt thereof is as follows:

| Ingredients | Amount (parts by weight) |
|---|---|
| etoposide | 1 |
| polyethylene glycol | 1-10 |
| sodium taurocholate | 1-10 |
| dimethylisosorbide | 1-10 |
| acid | 0.005-0.5 |
| water | 0.1-2 |

A further preferred embodiment of an etoposide solution in dimethylisosorbide containing taurocholic acid or a pharmaceutically acceptable salt thereof is as follows:

| Ingredients | Amount (parts by weight) |
|---|---|
| etoposide | 1 |
| polyethylene glycol | 1-10 |
| sodium taurocholate | 1-10 |
| dimethylisosorbide | 1-10 |
| organic carboxylic acid | 0.005-0.5 |
| ethanol | 0.1-2 |
| water | 0.1-2 |
| buffer | 0.005-0.5 |
| surfactant | 0.05-1 |

A more preferred embodiment of an etoposide solution in dimethylisosorbide containing taurocholic acid or a pharmaceutically acceptable salt thereof is as follows:

| Ingredients | Amount (parts by Weight) |
|---|---|
| etoposide | 1 |
| polyethylene glycol 300 | 1-10 |
| sodium taurocholate | 1-10 |
| dimethylisosorbide | 1-10 |
| glycerin | 0.1-2 |
| citric acid | 0.005-0.5 |
| ethanol | 0.1-2 |
| water | 0.1-2 |
| sodium acetate | 0.005-0.5 |
| poloxamer surfactant | 0.05-1 |

A most preferred embodiment of an etoposide solution in dimethylisosorbide containing taurocholic acid or a pharmaceutically acceptable salt thereof is as follows:

| Ingredients | Amount (parts by weight) |
|---|---|
| etoposide | 1 |
| polyethylene glycol 300 | 3.35 |
| sodium taurocholate | 2 |
| dimethylisosorbide | 2 |
| glycerin | 0.6 |
| citric acid | 0.1 |
| ethanol | 0.4 |
| water | 0.4 |
| sodium acetate | 0.05 |
| poloxamer (Pluronic F-127) | 0.1 |

PROPERTIES OF ETOPOSIDE COMPOSITIONS

I. Etoposide in dimethylisosorbide

A typical solution containing 50 mg/ml etoposide and 4 mg of citric acid in dimethylisosorbide is subjected to accelerated temperature testing. The results as shown in Table II indicate that the solution is satisfactorily stable at elevated temperature for a prolonged period of time.

TABLE II

| Stability of Etoposide in Dimethylisosorbide (50 mg/ml) | | |
|---|---|---|
| Temperature | Time | % Loss |
| 70° C. | 1-week | 0 |
| 70° C. | 2-weeks | 11.0 |
| 56° C. | 2-weeks | 0 |
| 56° C. | 4-weeks | 1.0 |
| 56° C. | 8-weeks | 1.0 |
| 45° C. | 4-weeks | 0 |

A solution of etoposide in dimethylisosorbide containing 50 mg of etoposide activity per ml showed no precipitation of etoposide for 24 hours after dilution with aqueous parenteral vehicles to an etoposide concentration of 0.4 mg/ml. Table III sets forth results obtained from stability studies upon dilution with 0.9% NaCl injection or Water for Injection U.S.P. and demonstrates the satisfactory crystallization utility time (time when onset of crystallization is noted) of the etoposide in DMI solution.

TABLE III

Physical Stability of Etoposide Injection Formulations In Dimethylisosorbide Upon Dilution in Aqueous Media

| Diluent | Conc. of Etoposide | Time | Physical Observation Formulation 1* | Formulation 2* |
|---|---|---|---|---|
| 0.9% Sodium Chloride Injection, U.S.P. | 0.4 mg/ml | 0 Hr | Clear | Clear |
| | | 4 Hr | Clear | Clear |
| | | 24 Hr | Clear | Clear |
| | | 48 Hr | Slight Haze | Slight Haze |
| Water for Injection, U.S.P. | 0.4 mg/ml | 0 Hr | Clear | Clear |
| | | 4 Hr | Clear | Clear |
| | | 24 Hr | Clear | Clear |
| | | 48 Hr | Slight Haze | Slight Haze |

*Formulation 1 contains (mg/ml): Etoposide (50), citric acid (4), DMI q.s. to 1 ml. Formulation 2 contains in addition 100 mg of highly purified Tween-80.

Etoposide in dimethylisosorbide, when administered parenterally, is preferably diluted with an appropriate volume of a parenteral vehicle to a concentration of about 0.4 mg/ml or lower of etoposide activity.

II. Etoposide and taurocholic acid in dimethylisosorbide

Etoposide in dimethylisosorbide solutions containing additionally sodium taurocholate were evaluated for delay in precipitation of etoposide after aqueous dilution. Each solution was subjected to two test methods, the procedures therefor are described below:

1. The sample (0.5 ml) was diluted with 0.1N HCl (5 ml) at 37° C. The diluted solution having a final etoposide concentration of approximately 10 mg/ml was placed in a shaker bath maintained at 37° C. The bath was set for gentle shaking and the test was carried out until significant precipitation of etoposide is visually evident.

2. The sample (4 ml) was diluted with water (200 ml) in a 1 liter dissolution vessel immersed in a water bath at 37° C. The mixture was stirred at 50 rpm with a USP paddle until significant precipitation of etoposide was visually evident.

The results are presented below in Table IV:

TABLE IV

Delayed precipitation of etoposide after aqueous dilution at 37° C.

| Ingredients | Formulation I | Formulation II | Formulation III |
|---|---|---|---|
| Etoposide | .0500 g | .0500 g | .0500 g |
| Citric acid anhydrous | .0050 g | .0050 g | .0050 g |
| Sodium acetate | .0025 g | .0025 g | .0025 g |
| PEG 300 | .1675 g | .1725 g | .1675 g |
| glycerin | .0300 g | .0300 g | .0300 g |
| ethanol, absolute | .0200 g | .0200 g | .0200 g |
| water, purified | .0200 g | .0200 g | .0200 g |
| sodium taurocholate | .1000 g | .1000 g | .1000 g |
| DMI | .1000 g | .1000 g | .1000 g |
| Pluronic F68 ® | — | — | .0050 |
| Pluronic F127 ® | .0050 | — | — |
| Total net weight | .5000 g | .5000 g | .5000 g |
| Precipitation delay (min.) | | | |
| Test 1 | 55 | 45 | 45 |
| Test 2 | 120 | 55 | Not tested |

In contrast, the etoposide solution currently used as fill for capsules having the composition 0.0500 g etoposide, 0.0010 g citric acid, 0.0410 g glycerin, 0.0390 g purified water, and 0.5440 g PEG 400 (total net weight 0.6750 g) showed immediate precipitation of etoposide in both tests. Thus, an advantage of the preparations containing taurocholic acid or a salt thereof is the significant delay in etoposide precipitation upon aqueous dilutions.

A further advantage of the etoposide in dimethylisosorbide solution containing taurocholic acid or a salt thereof over the current formulation for capsule fill is the significant reduction of capsule fill weight. This reduction will in turn enable capsules of decreased size to be produced.

The solution of the present invention may be administered in substantially the same manner as known etoposide compositions. The actual preferred dosage of etoposide administered orally or parenterally in a composition of the present invention will be at the discretion of the skilled clinical oncologist, and will vary according to the type of tumor being treated, route of administration, severity of disease, patient characteristics, etc.

The following examples serve to illustrate the present invention and do not limit the scope of the invention.

EXAMPLE 1

Twenty-four g of anhydrous citric acid was dissolved in 650 ml of DMI by stirring at 24° C. Three-hundred g of etoposide was added to the solution and the mixture stirred until etoposide was completely dissolved. The volume of the solution was brought up to 1000 ml by DMI and stirring was continued for an additional 10 minutes. The resulting solution contained 300 mg/ml etoposide activity. The solution was passed through a 0.45 micron membrane filter and the filtrate collected in a suitable clean container. The solution was filled into soft gelatin capsules.

EXAMPLE 2

Solutions of different etoposide concentrations are prepared if the procedure of Example 1 is repeated using the amount of citric acid and etoposide listed below.

| Citric Acid (g) | 20 | 16 | 8 | 4 |
|---|---|---|---|---|
| Etoposide (g) | 250 | 200 | 100 | 50 |
| DMI (ml) | - q.s. to 1000 ml - | | | |
| Etoposide Concentration (mg/ml) | 250 | 200 | 100 | 50 |

EXAMPLE 3

One g of etoposide was dissolved in 2 g of dimethylisosorbide. Four-hundred mg of water, 400 mg of absolute ethanol and 600 mg of glycerin was added to the solution and stirred until visually uniform. Two g of sodium taurocholate, 100 mg of anhydrous citric acid, and 50 mg of sodium acetate was added to the solution and the mixture was stirred until a clear solution formed. One hundred mg of Pluronic F127® was added to the solution and the weight was brought up to 10 g with polyethylene glycol 300. The mixture was stirred until visually uniform and then filled into capsules.

What is claimed is:

1. An etoposide solution comprising etoposide in dimethylisosorbide.

2. A solution of claim 1 which further comprises a pharmaceutically acceptable acid.

3. A solution of claim 2 wherein said acid is an organic carboxylic acid.

4. A solution of claim 2 wherein said acid is citric acid.

5. A solution of claim 1 or claim 2 or claim 3 or claim 4 wherein said solution is encapsulated within a hard gelatin capsule.

6. A solution of claim 1 or claim 2 or claim 3 or claim 4 wherein said solution is encapsulated within a soft gelatin capsule.

7. A solution of claim 6 wherein said solution contains from about 50 mg to about 320 mg etoposide activity per ml.

8. A solution of claim 2 wherein said solution contains from about 0.01 to about 0.2 part by weight of said acid per part by weight of etoposide.

9. A solution of claim 1 wherein the solution contains from about 50 mg to about 320 mg etoposide activity per ml.

10. A solution of claim 1 wherein the solution contains from about 10 mg to about 50 mg etoposide activity per ml.

11. A sterile solution of claim 1 adapted for sterile parenteral administration upon dilution with a parenteral vehicle.

12. A solution of etoposide in dimethylisosorbide containing from about 50 mg to about 320 mg etoposide activity per ml and from about 0.01 to about 0.2 part by weight of a pharmaceutically acceptable organic carboxylic acid per part by weight of etoposide.

13. A solution of claim 12 wherein the acid is citric acid.

14. A solution of claim 13 wherein the amount of citric acid is from about 0.05 to about 0.1 part by weight per part by weight by weight of etoposide.

15. A solution of claim 13 wherein the amount of citric acid is about 0.08 part by weight per part by weight of etoposide.

16. A solution of claim 12 wherein said solution is encapsulated within a soft gelatin capsule.

17. An etoposide solution which comprises etoposide, taurocholic acid or a pharmaceutically acceptable salt thereof, polyethylene glycol, water, a pharmaceutically acceptable acid, and dimethylisosorbide.

18. A solution of claim 17 which further comprises a lower alcohol.

19. A solution of claim 18 wherein said lower alcohol is ethanol.

20. A solution of claim 19 which further comprises glycerin.

21. An etoposide solution which comprises etoposide, taurocholic acid or a pharmaceutically acceptable salt thereof, polyethylene glycol, water, a pharmaceutically acceptable acid, ethanol, glycerin, a buffer, and dimethylisosorbide.

22. A solution of claim 17 wherein said solution contains for each part by weight of etoposide, 1–10 parts by weight of polyethylene glycol, 1–10 parts by weight of taurocholic acid or a pharmaceutically acceptable salt thereof, 1–10 parts by weight of dimethylisosorbide, 0.005–0.5 parts by weight of a pharmaceutically acceptable acid, and 0.1–2 parts by weight of water.

23. A solution of claim 21 wherein said solution contains for each part by weight of etoposide, 1–10 parts by weight of polyethylene glycol, 1–10 parts by weight of taurocholic acid or a pharmaceutically acceptable salt thereof, 1–10 parts by weight of dimethylisosorbide, 0.005–0.5 parts by weight of a pharmaceutically acceptable acid, 0.1–2 parts by weight of glycerin, 0.1–2 parts by weight of ethanol, 0.005–0.5 parts of a buffer, and 0.1–2 parts by weight of water.

24. A solution of claim 22 wherein said polyethylene glycol has a molecular weight of about 300, and said pharmaceutically acceptable acid is citric acid.

25. A solution of claim 23 wherein said polyethylene glycol has a molecular weight of about 300, said pharmaceutically acceptable acid is citric acid, and said buffer is sodium acetate.

26. A solution of claim 17 which further comprises a surfactant.

27. A solution of claim 26 wherein said surfactant is a poloxamer.

28. A solution of claim 26 wherein said poloxamer is poloxamer 407.

29. A solution of claim 23 which further comprises for each part by weight of etoposide, 0.05 - one part by weight of a surfactant.

30. A solution of etoposide which comprises:
   (a) 1 part by weight of etoposide;
   (b) 0.1 part by weight of citric acid;
   (c) 0.05 part by weight of sodium acetate;
   (d) 0.335 part by weight of polyethylene glycol 300;
   (e) 0.6 part by weight of glycerin;
   (f) 0.4 part by weight of ethanol;
   (g) 0.4 part by weight of water;
   (h) 2 parts by weight of taurocholic acid or a pharmaceutically acceptable salt thereof;
   (i) 2 parts by weight of dimethylisosorbide;
   (j) 0.1 part by weight of poloxamer 407.

31. A soft gelatin capsule containing as a fill an etoposide solution of claim 17.

32. A soft gelatin capsule containing as a fill an etoposide solution of claim 21.

33. A soft gelatin capsule containing as a fill an etoposide solution of claim 27.

34. A soft gelatin capsule containing as a fill an etoposide solution of claim 28.

35. A soft gelatin capasule containing as fill an etoposide solution of claim 29.

* * * * *